United States Patent [19]
Wahi

[11] Patent Number: 5,674,481
[45] Date of Patent: *Oct. 7, 1997

[54] ELECTROSTATICALLY CHARGED NASAL TOPICAL APPLICATION PRODUCT

[76] Inventor: Ashok L. Wahi, 628 E. Brookside La., Somerville, N.J. 08876

[*] Notice: The term of this patent shall not extend beyond the expiration date of Pat. No. 5,468,488.

[21] Appl. No.: 560,659

[22] Filed: Nov. 20, 1995

Related U.S. Application Data

[63] Continuation-in-part of Ser. No. 80,775, Jun. 24, 1993, Pat. No. 5,468,488.

[51] Int. Cl.$^6$ .............................. A61K 9/10; A61K 9/70
[52] U.S. Cl. .................. 424/78.03; 424/43; 424/401; 424/443; 424/484; 514/937; 514/944; 514/969; 128/205.27
[58] Field of Search ................ 424/78.03, 43, 424/401, 484, 443; 514/937, 944, 969; 128/205.27

[56] References Cited

U.S. PATENT DOCUMENTS 5,468,488  11/1995  Wahi ..................... 424/78.03

*Primary Examiner*—Raj Bawa
*Attorney, Agent, or Firm*—Kenneth P. Glynn, Esq.

[57] ABSTRACT

This is a product and method for restricting the flow of airborne contaminants into a nasal passage. It involves creating an electrostatic field in an area near a nasal passage. The electrostatic field may either repel or attract airborne contaminants or both. The product may take the form of a plurality of masses of one or more electrostatic materials, the masses have an average cross sectional area of about one square millimeter to about 50,000 square millimeters, the mass being of sufficient charge to create an electrostatic field which will prevent at least some airborne contaminants from passing into a nasal passage. There is also a carrier material with the plurality of masses dispersed therein. The product may be a topical solution, a semi solid, a solid, a spray solution or a vaporizable solution. Alternatively, it may be in a form which includes a substrate for the carrier and, in one preferred embodiment, the substrate would be an adhesive material such as a bandage.

11 Claims, 2 Drawing Sheets

ELECTROSTATIC MATERIAL CREATING FIELD
IN AREA OF NASAL PASSAGES

1.) SOLID-FLEXIBLE, SEMIRIGID, RIGID
2.) FOAM-FLEXIBLE, SEMIRIGID, RIGID
3.) SEMISOLID, GEL, HYDROGEL
4.) SOLUTION-OINTMENT, CREAM, PASTE, SOL
(A) WITH OR WITHOUT CARRIER
(B) WITH OR WITHOUT SUBSTRATE
(C) WITH OR WITHOUT ADHESIVE

ELECTROSTATICALLY CHARGED NASAL TOPICAL APPLICATION PRODUCT

REFERENCE TO RELATED CASE

This application is a continuation-in-part of currently U.S. patent application Ser. No. 08/080,775, filed on Jun. 24, 1993, now U.S. Pat. No. 5,468,488,by Ashok L. Wahi and entitled Electrostatically Charged Nasal Application Product and Method.

BACKGROUND OF THE INVENTION

1. Field of the Invention

The present invention is directed to products for restricting the flow of airborne contaminants into a nasal passage. More particularly, it is directed to such a product which includes the ability to create an artificial electrostatic field in an area close to, at, or within the nasal passage to either repel or attract airborne contaminants, or both, to prevent such contaminants from entering the nasal passage and body of a user.

2. Information Disclosure Statement

Electrical fields exist in all spaces which interact with airborne charges, particulates, water droplets and absorbed gases. In other words, electrical fields are all around us. Thus, even around the human body, there is a naturally occurring electrostatic field which may be dependant upon a number of factors. The intensity and charge of the field is dependant upon what the person is wearing, the relative humidity, the air content, the temperature and other factors. Additionally, man made environmental considerations seriously affect electrical fields around the human body. Thus, electrical wires, lighting, computer terminals, televisions, radios, transmitters, electric razors, hair dryers, humidifiers, air conditioners, heaters, electric blankets and many other man made external devices will affect a charge about the human body. However, notwithstanding the fact that the body will typically have an electrical field about it, including in the general area of nasal passages, airborne contaminants enter nasal passages and enter into the body to seriously impact upon many individuals. Thus, there is industrial and chemical pollution which may have short term and certainly has perceivable long term effects on many individuals. Additionally, there are natural pollutants such as various types of pollens and spores which cause allergies and, in severe cases, will have a major impact upon the human bodies ability to function in a normal fashion.

Attempts to protect the human body and especially the nasal passages of people who are exposed to various airborne contaminants have taken many forms. These include structures which attempt to remove contaminants on a macro scale. Thus, we have homes, vehicles, offices and other complexes and even enclosed malls which have major air filters which may be mechanical and/or electrostatic. Many homes today are built with electrostatic precipitators as part of the heating and air conditioning systems. In addition to building-wide attempts to remove contaminants and pollutants from the air, room deodorizers and air filters have been promoted and are recognized to remove some contaminants. Such devices, however, may or may not attract the contaminants and remove them after they have passed before individuals in the room. Finally, on the personalized level, air filter masks and other mechanical filters have been proposed but are recognized as extreme attempts to remove contaminants and are also beamed as cumbersome and antisocial.

In addition to attempts to remove airborne contaminants to reduce the intake of such contaminants, one significant alternative approach is to treat the human body after the contaminants have entered the body. This is not a preventive approach, but rather an after the fact attempt to minimize or eliminate the effects of the contaminants and pollutants. Thus, many people today take hay fever medications, sinus medications and allergy medications for this purpose. The problem with the pharmaceutical approach is that it does not prevent the damage done by the airborne contaminants but rather removes or reduces some of the results.

Notwithstanding the significant attempts over the decades to reduce human exposure to airborne contaminants, many people today continue to be exposed to natural and man-made contaminants and suffer significantly. Further, the prior art neither teaches nor suggests the present invention approach to the problem which is unique and different from all others, that is, the creation of an artificial electrostatic field in the area near the nasal passage to repel and/or attract airborne contaminants and to thereby prevent such contaminants from entering the nasal passage.

SUMMARY OF THE INVENTION

The present invention is a product for restricting the flow of airborne contaminants into a nasal passage. It involves, in its most general terms, means for creating an electrostatic field in an area near a nasal passage. The electrostatic field may either repel or attract airborne contaminants or both. The product may take the form of a plurality of masses of one or more electrostatic materials, the masses have an average cross-sectional area of about one square millimeter to about 50,000 square millimeters, the mass being of sufficient charge to create an electrostatic field which will prevent at least some airborne contaminants from passing into a nasal passage. Also included in these embodiments would be a carrier material with the plurality of masses dispersed there through. The product may be a topical solution, a semisolid, a solid, a spray solution or a vaporizable solution. Alternatively, it may be in a form which includes a substrate for the carrier and, in one preferred embodiment, the substrate would be an adhesive material such as a bandage. The present invention also includes methods of preventing airborne contaminants from entering nasal passages utilizing the aforesaid products.

BRIEF DESCRIPTION OF THE DRAWINGS

The present invention will be more fully understood when the disclosure herein is taken in conjunction with the drawings appended hereto, wherein;

FIG. 1 shows schematically the product concept of the present invention;

DETAILED DESCRIPTION OF THE PRESENT INVENTION

Figure 2:
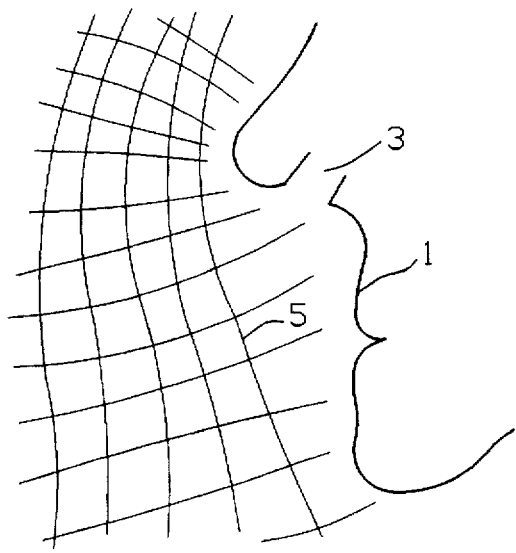
FIG. 2 shows a side partial stylized view of a human illustrating a typical electrostatic field around a human nasal passage.

The present invention is primarily directed to the prevention of harmful effects caused by airborne contaminants which enter the human nasal passage during breathing. As mentioned in the background above, the prior art is lacking in means for protecting the human from harmful effects of airborne contaminants in a practical manner rather than treating the affects of such contaminants. Thus, in its broadest sense, the present invention is directed to the creation of an artificial electrostatic field in an area near a human nasal passage. The present invention product may be in the form of a solution, a semisolid or a solid. The solution may be a topical solution, a spray solution or a vaporizable solution. Semisolids may take the form of an ointment, a paste, a cream or a gel. A gel may likewise be in the form of a spreadable gel or a hydrogel.

In one preferred embodiment of the present invention, the electrostatic material constitutes the means for creating the electrostatic field and need not be dispersed within a carrier or applied to a substrate. For example, the electrostatic material itself may be a polymeric material which could come in the form of a flexible, semirigid or rigid strip which could have an adhesive applied to one side for adhering to a facial area near a nasal passage. Alternatively, the electrostatic material could be a flexible, semirigid or rigid, open pore or closed pore foam which, in and of itself would not require any carrier or substrate and could include adhesive for attachment to a facial area.

In preferred embodiments, the present invention product may be applied in its particular physical form directly to a nasal passage or in the area of a nasal passage for example, by using the finger or by using an applicator which may be provided by the manufacturer. Thus, the present invention product may take the form of a carrier with the active electrostatic material dispersed throughout at least a portion of the carrier. Thus, the electrostatic material may be a plurality of masses of one or more electrostatic materials. These masses have an average cross-sectional area of about 1 square millimeter to about 50,000 square millimeters and are sufficient to create such an electrostatic field which will prevent at least some airborne contaminants from entering into a human nasal passage.

In other preferred embodiments, the present invention product includes the aforementioned carrier and active material, as well as a substrate. The substrate may be one which could be attached to the face or nasal area in general and may be rigid or flexible, but it is preferably flexible and includes adhesive material and thus may take the form of something similar to a bandaid. In other words, a flexible substrate may hold the carrier with the active material dispersed therein and this flexible substrate will advantageously have adhesive material for adherence at or near the nasal passages.

The plurality of masses of one or more electrostatic materials is created by combining one or more electrostatic materials with an appropriate carrier. These electrostatic materials may be organic or inorganic such as polymers, salts, ionic compounds, compound ionic/compound non-ionic mixtures, copolymers having hydrophobic and/or hydrophilic linkages etc. Among the specific electrostatic materials which may be used in the present invention are: Quarternary Cellulosic Derivatives, Quarternary Ammonium Compounds, Quarternized Proteins, Fatty or Polymer derived Quarternary Ammonium Compounds, and their equivalents.

The carrier used in the present invention may be a single material or a combination of materials and the choice of carrier depends upon the physical form of the present invention product desired. Thus, the carrier will depend on whether or not one desires a liquid, a solid or a semisolid, whether the liquid is to be sprayed, vaporized or applied with an applicator, whether or not the semisolid is to be in paste or cream or ointments or other form; whether or not the solid material is to be flexible or rigid or semi flexible.

Thus, the carrier may be taken from many different materials or combinations of materials and may include other ingredients which would enhance the carrier and/or electrostatic materials.

When ointments are desired, hydrocarbon-based semisolids containing dissolved or suspended electrostatic materials may be used. These typically contain fluid hydrocarbons having about 16 to about 30 carbon atoms and may be straight chained or branched. Other semisolid hydrocarbons may involve entrapment of particulate electrostatic materials and may have from 30 to 50 carbons and likewise may be straight chained or branched.

The preparation of the present invention product which is in the form of ointments simply involves the preparation of the ointment material which may involve melting various waxes and/or oils and crystallizing followed by physically mixing the electrostatic materials therein. Such semisolids include petroleum distillates which act as typical ointments macroscopically. Commercially available mineral oil bases which are gelled with polyethylene may be useful in the present invention, as may other hydrocarbon ointments. Also useful are silicone based ointments and these may contain polysiloxanes to impart wax like or ointment like properties. Likewise, polyethylene glycol ointments may be used and short chain polyethylene glycol polymers are well known as well as long chain polyethylene glycol polymers, depending upon the particular feel and consistency of the product. Water-in-oil emulsions may likewise be created to have an ointment which would include electrostatic materials of the present invention. Additives to emulsify water, including cholesterol, lanolin, semi synthetic lanolin derivatives and various ionic and non-ionic surfactants may be included alone or in combination.

Additionally, the present invention product may take the form of a paste and these are basically ointments which have a higher percentage of insoluble solids. Such insoluble solids may comprise as much as 50 percent by weight and render the pastes stiffer than the ointments due to the presence of these solids. Ingredients such as starch, zinc oxide, calcium carbonate, talc and other somewhat inert particulate may be added to the typical ointment materials to create pastes which are useful in the present invention. By virtue of the inclusion of particulate materials therein, the pastes may be less greasy than the ointments and may have a better feel and are less likely to be accidentally removed or otherwise deteriorated through exposure to weather or otherwise. The present invention product may also take the form of a cream and the use of the word cream is generally recognized in the pharmaceutical and related arts to take the form of ointments which have a white appearance, although the term has been applied to both absorption bases containing emulsified water and to semisolid systems. Nonetheless, creams may contain lipids and other moisturizers and might include nonvolatile water-miscible solvents such as polyethylene glycol. They may also include solubilized waxy acids and wax like materials. Thus, creams may contain long chain alcohols, long chain esters and long chain acids such as cetyl alcohol, stearyl alcohol and myristate alcohols, palmitate alcohols and stearate alcohols, as well as palmitic acid and stearic acid. Additionally, vegetable and animal oils and assorted waxes may be included to form creams used in the present invention products.

Gels may be used in the present invention products and these are semisolid systems in which a liquid phase is constrained within an interlocked three dimensional polymeric matrix of a natural or synthetic polymers such as a natural or synthetic gum. Typically, significant physical or chemical cross linking or interweaving is involved. Gel chemistry is now well established and hydrogels are well known for the application of facial makeup formulations. Hydrogels may include bases of many different types of organic materials and including carrageen, agar, pectin, methylcellulose, hydrocellulose, carboxymethylcellulose, polyacrylonitrile polymers etc. These gels may either be spreadable gels in the sense of being very small groupings of polymers in the semisolid system which render the gels easily spreadable or they may be microencapsulations which are separate from one another or macroencapsulations which could form a layer of material which may or may not be spreadable. Thus, spreadable gels would be referred to herein as gels whereas nonspreadable gels would be referred to herein as hydrogels.

In addition to the above, the present invention product may be in the form of a flexible, semiflexible or rigid foam based carrier and an electrostatic material. Again, the chemistry of creating foams is well known and the electrostatic materials may be intricately formed therewith or added thereto afterward by physical incorporation.

The present invention carriers may take the form of materials which could be in the liquid or semisolid phase and may be vaporizable or sprayable. Sprayable solutions may well be suspension systems and may include various alcohols such as ethyl alcohol, glycols and water and may include solubilizers or surfactants as well as antioxidants, as needed. Propellants are used with aerosol solutions and propellants are well known in the industry.

In those embodiments wherein the present invention product is applied to a substrate, the product may contain electrostatic materials which have size considerations based directly on the nature of the substrate to be used. Thus, foam substrates should have small enough electrostatic materials within the carriers to allow significant electrostatic material to be spread into foam open cells with sufficient carrier to create significant electrostatic charge.

Likewise, whether the present invention product is on a substrate or simply used in its carrier and applied directly, there may be one or more masses of electrostatic fields and the charges may be positive, negative or combination of both positive and negative charges. One interesting embodiment would be to have a matrix of squares, rectangles, circles or other random configurations where positive and negative charge groupings alternate.

EXAMPLE #1

| Ingredient | % age composition by weight |
|---|---|
| 1. Deionized Water | 80.9 |
| 2. Potassium Sorbate | 0.1 |
| 3. Celquat SC 240 C | 3.9 |
| 4. Polawax 5% in water | 4.9 |
| 5. Agestat 400 | 7.9 |
| 6. Arlacel 165 | 1.0 |
| 7. Tween 60 | 0.1 |
| 8. Propylene Glycol | 1.2 |
| | 100.0 |

EXAMPLE #2

| Ingredient | % age composition |
|---|---|
| 1. Deionized water | 78.5 |
| 2. Celquat SC 240 C | 3.8 |
| 3. Agestat 400 | 7.6 |
| 4. Polawax 5% in water | 9.5 |
| 5. Potassium Sorbate | 0.1 |
| 6. Necon LO | 0.5 |
| | 100.0 |

EXAMPLE #3

| Ingredient | % age composition |
|---|---|
| 1. Deionized water | 89.9 |
| 2. Celquat SC 240 C | 4.0 |
| 3. Agestat 400 | 6.0 |
| 4. Potassium Sorbate | 0.1 |
| | 100.0 |

Generic/Chemical name of the above ingredients are:
Celquat SC 240 C; Quarternary Cellulosic Derivative
Polawax; Fatty Alcohol, Polysorbate Blend
Agequat 400; Poly(Dimethyl Diallyl Ammonium Chloride)
Arlacel 165; Glycerol Monostearate and Polyoxyethyline Stearate
Necon LO; A surfactant
Tween 60; Polysorbate
Propylene Glycol; 1,2-Propane Diol Brief Process of Formulation:

In all of the above Examples, the ingredients are added one by one, at room temperature, in the order listed to water, while stirring. No new ingredient is added until the one added before was dispersed completely. Polawax and Arlacel were dispersed by warming the mixture, to 60 degrees C., over a water bath. After all ingredients were added, the contents were mixed well for uniformity, let cool to room temperature and bottled.

EXAMPLE 4

Patients were provided with 0.5 ounce samples of the gel prepared by Example 1 for testing during the months of September and October 1995. Of these patients, ten were willing to and did apply the gel around the nasal passages. All of these patients had a history of allergic rhinitis with different symptoms of nasal congestion, runny nose, sneezing, nose irritation, throat irritation, and had a history of seasonal exacerbations. All of these patients were using different medications for temporary relief of symptoms.

Each patient was provided with the gel along with directions for use which included that a very thin film should be applied with the finger on the outside of the nostril and above the upper lip and to repeat the application four times a day. In the case of a runny nose, the patient was supposed to blow, rinse, and dry nose before applying the gel. All patients were instructed to avoid contact with eyes. During the period of use of the gel, patient was instructed not to use other anti-allergy medicine including antihistamines, steroids, or over the counter drugs. Patients used the gel for four days.

Seven patients reported significant improvement in their symptomology. An eighth patient noticed little improvement and two patients did not notice any effect. Thus, 70% of the patients experienced significant improvements with respect to allergic rhinitis symptoms.

The present invention product is applied at or near the nasal passage by either being attached to the face externally or being placed within the accessible regions of the nasal passages. These areas shall be taken to include one or more areas of:

(a) within the nasal passages;

(b) at the outer edges of the nasal passages;

(c) on the skin or tissue areas around the outside of the nasal passages including the nose and areas above the upper lip, as well as the upper lips; and, (d) any combination of these areas.

The electrostatic material will be operable for a predetermined time or for a predetermined quantity of contaminants to be attracted. The present invention product may subsequently be removed once it is used up, for example, by being wiped away or may just wear away through material functions, incidental wipings, other touchings and routine washing habits. Alternatively, in the case of a patch or bandage or substrate material, the carrier may be placed strategically in the nasal passage or on the face or across the nose as desired or recommended and may then be removed after a predetermined period of time and replaced with a fresh product. The present invention product is formulated to, as mentioned, have adequate electrostatic charge to prevent at least some airborne contaminants from entering the nasal passages and to cause harmful affects on the user. Typically, the electrostatic charge will have a minimum desired initial charge of $10^{-8}$. Typically, the electrostatic field will have a charge in the range of $10^{-9}$ and $10^{-3}$. While these ranges are quantified, it should be recognized that highly concentrated product will require a small surface area or application and thus may have a greater charge than the ranges set forth herein and, likewise, for materials that are spread over large surface areas, such as around the cheeks, above the upper lip, and over the nose, the charge for square millimeter may be significantly less and yet still may be effective to achieve the objectives of the present invention.

Referring now to FIG. 1, there is shown a block diagram which summarizes the present invention parameters. Basically, shown in block 101, is the electrostatic material creating a field in the area of nasal passages. The electrostatic material may be solid, foam, semisolid, gel, hydrogel, a solution, an ointment, a cream, a paste or sol. The solution may be a liquid or a dispersion, one for spray application or even vaporization. The electrostatic material may be used alone or with a carrier. "Carrier" is described above as taken to mean a somewhat fluid material into which electrostatic material may be dispersed. The electrostatic material may be with or without a substrate, that is with the electrostatic material applied directly to a substrate or in a carrier and then applied to a substrate. Finally, the product of the present invention with the electrostatic material for creating the field in the area of nasal passages may be with or without an adhesive. If it is in a solid form which is rigid or semirigid or like a flexible tape or bandage, then an adhesive may be necessary for maintaining the product in the area of the nasal passages.

FIG. 2 shows a partial side stylized view of a face 1 including a nasal passage 3. This facial representation is repeated in FIGS. 3, 4, and 5 and like parts are like numbered and will not be repeated in the discussion below.

As shown in FIG. 2, an electrostatic field is represented as typical by grid 5. Grid 5 simply represents electrostatic charged concentration with some fixed but arbitrary number of charges of ionically charged pollutants per grid block. Thus, if the grid blocks are larger, the electrostatic charge is smaller and if the grid blocks are smaller, the electrostatic charge is larger because there are more charges in a given area.

Figure 3:
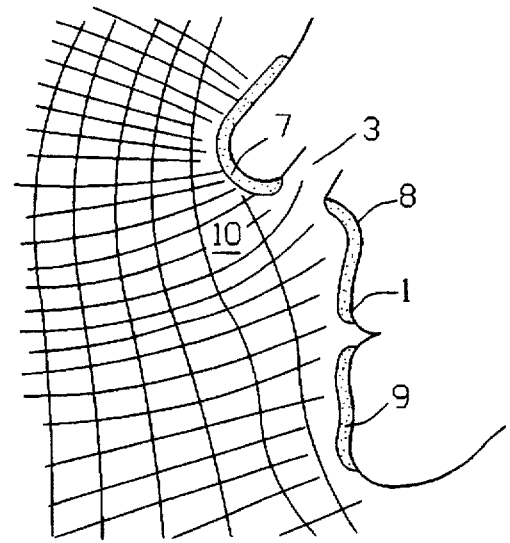
FIG. 3 shows the same stylized human outline as in FIG. 2 but with an artificially created electrostatic field near a persons nose to restrict the flow of airborne contaminants into the nasal passages.

FIG. 3 represents one possible arrangement for a present invention product. Here, face 1 includes the application of a cream or paste product of the present invention which is developed to attract pollen as a result of the electrostatic charge. The cream or paste is applied in areas 7, 8 and 9, that is, over the nose, above the lips, and in the chin and face area. As a result, a large concentrated grid 10 is shown, which has an artificial electrostatic field of much higher concentration than the typical field shown in FIG. 2. As a result, the airborne contaminants such as pollen will be attracted to and adhere to the cream or paste and, once the cream or paste is loaded with ionically charged pollutants, for example, after four hours of use, the cream or paste may be wiped off and new material applied.

Figure 4:
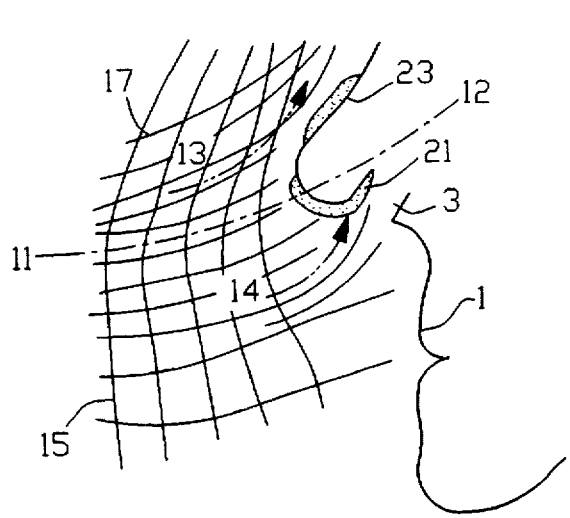
FIG. 4 shows another alternative present invention embodiment wherein a combination of artificially created electrostatic fields are shown; and, FIG. 5 shows a mild artificially created electrostatic field.

FIG. 4 shows an alternative embodiment where two different types of ointments are used. Here, ointment 21 is positively charged and is applied to the mucus membrane of the nasal passage area directly while ointment 23 is negatively charged and is applied to the nose, as shown. As a result, there is a positive electrostatic grid 15 and a negative electrostatic field grid 17, as shown. Thus, below the line 11–12 is a positive field and above the line 11–12 is a negative field. Arrows 13 and 14 illustrate a feature of the present invention as shown in FIG. 4. Here, arrow 13 suggests that contaminants would be repelled by ointment 23, whereas, arrow 14 shows that similar contaminants would be attracted to ointment 21. This would be the case where the contaminants are essentially negatively charged.

Figure 5:
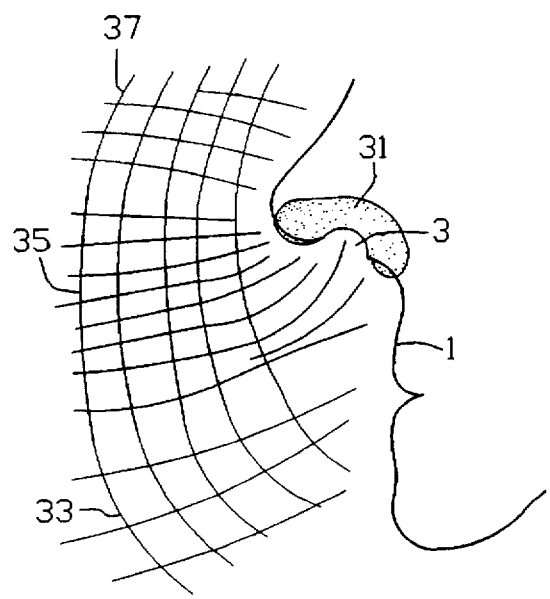

FIG. 5 shows yet another alternative present invention embodiment. Here, product 31 is a bandage material applied around the nasal area with a cut out or hole therein for nasal passage 3. This has a normal bandage material as substrate, with an adhesive against the skin areas and with an electrostatic material in a carrier on the outer surface of the bandage. Electrostatic grid 33 is a typical or normal electrostatic field grid as is grid 37. However, directly opposite product 31 is highly concentrated artificial electrostatic field 35 which, in this case, is to repel contaminants, attract contaminants or both. In one preferred embodiment, product 31 would be an array of squares, as shown thereon, wherein alternative squares would have positive and negative electrostatic fields so that airborne contaminants, whether negative or positive would migrate to product 31 and particularly to the area of its opposite charge, thereby preventing both positive and negative airborne contaminants from entering the nasal passage.

Obviously, numerous modifications and variations of the present invention are possible in light of the above teachings. It is therefore understood that within the scope of the appended claims, the invention may be practiced otherwise than as specifically described herein.

What is claimed is:

1. An nasal topical application product for restricting the flow of airborne contaminants into a human nasal passage by creation of an artificial electrostatic field near the human nose, wherein the nasal application product consists essentially of:

(a) a plurality of masses of one or more electrostatic polymers, each set of masses having an average cross-sectional area of about one square millimeter to about 50,000 square millimeters; and, (b) a topical carrier having said plurality of masses dispersed through a portion thereof.

2. The nasal application product of claim 1 wherein said product is selected from the group consisting of topical solutions, semisolids, spray solutions and vaporizable solutions.

3. The nasal application product of claim 1 wherein said product is selected from the group consisting of ointments, pastes, creams and gels.

4. The nasal application product of claim 1 wherein said carrier is selected from the group consisting of diluents, volatile spray carriers, lotions, solvents, gels and hydrogels.

5. The nasal application product of claim 1 wherein said carrier is a diluent selected from the group consisting of alcohols, glycerines, organic surfactants, esters being of unsaturated fatty acids, and mixtures thereof.

6. The nasal application product of claim 4 wherein said carrier is a volatile spray carrier selected from the group consisting of water, ethyl alcohols, natural oils, glycols, organic surfactants and mixtures thereof.

7. The nasal application product of claim 4 wherein said carrier is a lotion selected from the group consisting of polyethylene glycols, natural oils, silicones, waxes, and mixtures thereof.

8. The nasal application product of claim 4 wherein said carrier is a gel selected from the group consisting of three dimensional polymeric matrices of natural polymers, synthetic polymers, copolymers, and mixtures thereof.

9. The nasal application product of claim 1 wherein said product further includes a substrate containing said carrier with said plurality of masses of one or more electrostatic polymers dispersed through a portion thereof.

10. The nasal application product of claim 9 wherein said substrate is a flexible substrate having an adhesive thereon.

11. The nasal application product of claim 9 wherein said substrate is a bandage.

* * * * *